(12) United States Patent
Griffiths et al.

(10) Patent No.: US 6,248,695 B1
(45) Date of Patent: Jun. 19, 2001

(54) HERBICIDAL COMPOSITIONS

(75) Inventors: Paul Leslie Griffiths, Maribyrnong; Andrew Francis Kirby, Footscray; Stephen Patrick Tonner, Moonee Ponds, all of (AU)

(73) Assignee: Huntsman Surfactants Technology Corporation, Salt Lake City, UT (US)

( * ) Notice: Subject to any disclaimer, the term of this patent is extended or adjusted under 35 U.S.C. 154(b) by 0 days.

(21) Appl. No.: 09/319,337

(22) PCT Filed: Dec. 5, 1997

(86) PCT No.: PCT/AU97/00832

§ 371 Date: Jul. 19, 1999

§ 102(e) Date: Jul. 19, 1999

(87) PCT Pub. No.: WO98/24313

PCT Pub. Date: Jun. 11, 1998

(30) Foreign Application Priority Data

Dec. 6, 1996 (AU) .................................................. PO 4056

(51) Int. Cl.⁷ ............................. A01N 25/30; A01N 57/02
(52) U.S. Cl. .............................................................. 504/206
(58) Field of Search ................................................ 504/206

(56) References Cited

U.S. PATENT DOCUMENTS

| | | | |
|---|---|---|---|
| H224 | 3/1987 | Malik et al. | 71/92 |
| 4,159,901 | * 7/1979 | Beestman et al. | 71/86 |
| 4,414,158 | * 11/1983 | Thummel et al. | 71/86 |
| 5,789,345 | 8/1998 | Yasui et al. | 504/206 |
| 5,877,112 | * 3/1999 | Roberts et al. | 504/116 |

FOREIGN PATENT DOCUMENTS

| | | |
|---|---|---|
| B-58014/86 | 12/1986 | (AU) . |
| 64191/86 | 4/1987 | (AU) . |
| B-10350/92 | 8/1992 | (AU) . |
| 10067/97 | 7/1997 | (AU) . |
| 40 19 362 A1 | 1/1991 | (DE) . |
| 260 416 B1 | 3/1988 | (EP) . |
| 483 095 A2 | 4/1992 | (EP) . |
| 531 269 A2 | 3/1993 | (EP) . |
| 2 661 315 | 10/1991 | (FR) . |
| 2 289 408 | 11/1995 | (GB) . |
| 7-291832 | 11/1995 | (JP) . |
| WO 94/02021 | 2/1994 | (WO) . |
| WO 95/03697 | 2/1995 | (WO) . |
| WO 96/32839 | 10/1996 | (WO) . |

* cited by examiner

Primary Examiner—S. Mark Clardy
(74) Attorney, Agent, or Firm—Seed Intellectual Property Law Group PLLC

(57) ABSTRACT

This invention relates to a herbicidal composition comprising N-phosphonomethylglycine and/or a salt thereof and an alkyldiamine tetraalkoxylate surfactant, a surfactant composition useful in glyphosate compositions and a method for controlling or eradicating unwanted plants or vegetation.

18 Claims, 5 Drawing Sheets

HERBICIDAL COMPOSITIONS

This application has been filed under 35 USC 371 as a national stage application of international application PCT/AU97/00832 filed Dec. 5, 1997.

This invention relates to herbicide formulations, in particular to herbicide compositions comprising N-phosphonomethylglycine (glyphosate) herbicides and alkyldiamine tetraalkoxylate surfactants. The invention also relates to a surfactant composition comprising an alkyldiamine tetraalkoxylate surfactant and an alkyl glycoside or alkylpolyglycoside surfactant and its use with glyphosate herbicides, and to water soluble or water dispersible granules comprising a non-hygroscopic salt of glyphosate and a solid alkyldiamine tetraalkoxylate surfactant.

N-phosphonomethylglycine, commonly known as "Glyphosate", and its salts are well known non-selective systemic herbicides, first developed in the early 1970s by Monsanto Company. After absorption through the foliage it is rapidly translocated to regions of metabolic activity, including the roots and shoots. It has been found that formulation of glyphosate with some surfactant adjuvants can lead to enhancement of herbicidal activity.

Wyrill and Burnside, Weed Science Vol. 25 (1977), 275–287, conducted a study of the effects of different surfactants on the herbicidal action of glyphosate. Some classes of surfactant were more effective than others in enhancing the herbicidal effect of glyphosate (in particular as a solution of the isopropylamine salt).

Despite this study and subsequent attempts to correlate glyphosate activity enhancement with surfactant structure, the effectiveness of surfactants with glyphosate is variable and difficult to predict.

The most commonly used surfactant adjuvants in glyphosate formulations are the tallow amine ethoxylates. While these surfactants are very effective in enhancing the activity of glyphosate, they have recently been shown to have significant aquatic toxicity. Accordingly in many regions the use of glyphosate compositions comprising tallow amine ethoxylates in proximity to waterways and catchment areas has been severely regulated. In particular it has been shown that about 3 ppm of a standard ethoxylated tallow amine/glyphosate formulation has an acute toxic effect on *Daphnia carinata* according to a standard 48 hour $EC_{50}$ test.

It has now been surprisingly found that the use of alkyldiamine tetraalkoxylate as a surfactant in a glyphosate compositions provides glyphosate formulations with activity comparable to the known glyphosate/ethoxylated tallow amine compositions, and which exhibit low aquatic toxicity.

According to a first aspect of the present invention there is provided a herbicide composition comprising N-phosphonomethylglycine and/or a salt thereof and an alkyldiamine tetraalkoxylate surfactant.

As used herein, "glyphosate composition" means N-phosphonomethylglycine as well as any composition or formulation containing a glyphosate herbicide. "Glyphosate herbicide" means any form of glyphosate which in aqueous solution provides glyphosate anions along with suitable cations or glyphosate acid. Glyphosate herbicide includes the isopropylamine salts of glyphosate and other agriculturally acceptable salts of glyphosate such as those disclosed in U.S. Pat. No. 3,799,758.

Examples of such suitable cations are alkali metal cations, for instance sodium and potassium, and ammonium and substituted ammonium cations. The latter include cations derived from primary or secondary amines such as isopropylamine or dimethylamine, and from diamines such as ethylenediamine.

Further, examples of agriculturally acceptable salts of glyphosate are trimethyl-sulfonium salt ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the sodium, ammonium and trimethylsulphonium salts as well as the mixed alkylsulfonium salts and trialkyl salts.

It has been found that the surfactant adjuvants of the present invention have an efficacy which is comparable to the standard tallow amine ethoxylates currently in use. This is surprising since the hydrophobe in tallow amine is a mixture of fatty monoamines with a carbon chain link of 16 to 18 units. In contrast the base hydrophobe of the surfactants of the present invention is a diamine of a short $C_1$–$C_6$ alkyl chain. In addition the hydrophilic portions of the tallow amine contain only ethoxylate whereas the surfactant of the present invention may contain some higher alkoxylate groups.

In addition it would not be expected that the surfactants of the present invention would have a low toxicity profile from their structure. It is also unexpected that the surfactants of the present invention would perform as well as tallow amine as an adjuvant for glyphosate. All that the two hydrophobes have in common is an amine functionality, this amine functionality not having been previously identified as important for suitability for use with glyphosate. It has generally been considered that it is the alkyl chain function which is more important. It was therefore not expected that a short chain diamine would function as well as a long chain monoamine.

On the basis of their structure alkyldiamine tetraalkoxylate surfactants would not be expected to be compatible with the high salt and low pH environment of an aqueous glyphosate composition, and accordingly it is surprising that they are useful adjuvants for glyphosate herbicides.

The term "low aquatic toxicity" is used herein in connection with the surfactants or herbicide compositions of the present invention to refer to an acute aquatic toxicity less than the toxicity of an equivalent composition comprising an ethoxylated tallow amine as the surfactant component. The term also indicates that the toxicity of the surfactant or composition is sufficiently low to satisfy local, regional or national regulations governing the toxicity of surfactants or herbicide compositions in the locality, region or country in which the surfactant or composition is used. The herbicide compositions according to the present invention preferably meet a standard $EC_{50}$ or $LC_{50}$ test in respect of a suitable indictor organism, for example Daphnia species such as *Daphnia carinata*, at a concentration of 100 ppm, more preferably 300 ppm, and most preferably 1000 ppm.

In addition to the advantages of low aquatic toxicity and efficacy of alkyldiamine tetraalkoxylates as surfactants with glyphosate formulations, they also possess advantages over other surfactants which have been used with glyphosate formulations, such as ease of handling, and a lower foaming profile than some other surfactants currently used.

In a preferred embodiment the alkyldiamine tetraalkoxylate surfactant comprises a compound of formula (I):

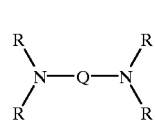

(I)

wherein Q is a linear or branched $C_1$–$C_6$ alkylene, and each R is independently selected from oxyalkylene polymer or block copolymer chains.

Q is preferably —$(CH_2)_n$— where in n is 2 to 6 or a branched alkylene group having 3 to 6 carbon atoms such as

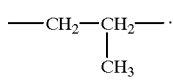

Most preferably Q is ethylene.

R may be a polymer of an oxyalkylene group such as oxyethylene, oxypropylene or oxybutylene. R may be a block copolymer of two or more different oxyalkylene groups such as oxyethylene, oxypropylene or oxybutylene. It is preferred that R is a block copolymer of oxyethylene and oxypropylene.

The blocks may alternative in the chain. For example compounds of formula (I) may be made by starting with a compound of formula (II):

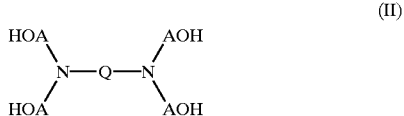

(II)

wherein A is an alkylene group. The compound of formula (II) may then be condensed with an alkylene oxide wherein the alkyl group may be the same or different to A. The resulting compound may be further condensed with a different alkylene oxide and so on to give the final compound.

In a further preferred embodiment, the surfactants of the present invention have the following formula (III):

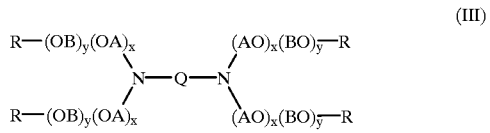

(III)

wherein A and B are different $C_2$–$C_4$ alkylene groups,

R is H or $C_1$–$C_6$ alkyl, and

X and Y are integers from 0 to 150, provided X and Y are not both zero.

Preferably A is propylene and B is ethylene, or A is ethylene and B is propylene.

Where A is propylene and B is ethylene, X is preferably an integer from 1 to about 30, more preferably about 4 to about 25, and Y is preferably 0 to about 150, more preferably about 4 to about 120.

Most preferred surfactants of the present invention are ethylene diamine alkoxylate of the following formula (IV):

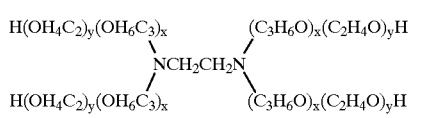

(IV)

wherein x and y are as defined above.

$C_2H_4O$ will hereinafter be referred to as EO and $C_3H_6O$ as PO.

Suitable alkyl diamine alkoxylates which may be used as surfactants are the SYNPERONIC T series and TERIC 173 which are commercially available ethylene diamine alkoxylates. Particularly suitable are SYNPERONIC T/304 and TERIC 173. SYNPERONIC T/304 and TERIC 173 are compounds of formula (IV) wherein x and y are 4. Also suitable are SYNPERONIC T/707 which is a compound of formula (IV) wherein x is 16 and y is 50, SYNPERONIC T/908 which is a compound of formula (IV) wherein x is 22.5 and y is 118 and TERIC 170 which is a compound of formula (IV) wherein x is 1 and y is 4.

It has been unexpectedly found that the incompatibility between the alkyldiamine tetraalkoxylate surfactant and glyphosate herbicide in concentrated solution can be overcome or alleviated by increasing the solubility of the surfactant by reducing the size of the oxyalkylene polymer or block copolymer chains. It is further surprising that in reducing the size of the oxyalkylene polymer or block copolymer chain that the efficacy and aquatic toxicity profile of the resulting formulations remains acceptable.

Accordingly in a second aspect the present invention provides a herbicide composition comprising N-phosphonomethylglycine and/or a salt thereof, and an alkyldiamine tetraalkoxylate surfactant, wherein the alkyldiamine tetraalkoxylate surfactant comprises a compound of formula (III) as defined above in which X and Y are integers from 0 to 5, provided X and Y are not both 0 and that X+Y is less than or equal to 6.

In a preferred embodiment of this aspect of the invention the alkyldiamine tetraalkoxylate surfactant comprises a compound of formula III where A is propylene, B is ethylene, R is hydrogen, X is 1 to 3, Y is 3 to 5, provided X+Y is 4 to 6.

In a particularly preferred embodiment X is 1 and Y is 4.

These alkyldiamine tetraalkoxylate surfactants have been found to be unexpectedly and surprisingly compatible with glyphosate in both low and high strength compositions. In particular the surfactants have been found to be compatible with horticultural/industrial type formulations (containing for example 360 g/l of glyphosate acid equivalent) and broad acre use formulations (containing for example 450 g/l of glyphosate acid equivalent).

It has also been surprisingly found that the incompatibility between the glyphosate herbicide and the alkylamine tetraalkoxylate surfactant can be overcome or alleviated by formulating the composition as a water soluble or water dispersible granule.

This involves using a non-hygroscopic salt of N-phosphonomethylglycine, such as an ammonium salt, together with a solid form of alkyldiamine tetraalkoxylate surfactant.

Accordingly in another aspect of the invention there is provided a herbicide composition in the form of water dispersible or water soluble granules comprising a non-hygroscopic salt of N-phosphonomethylglycine and an alkyldiamine tetraalkoxylate surfactant having a melting point or softening point greater than 45° C., preferably greater than 50° C.

It has been found that increasing the size of the oxyalkylene polymer or block copolymer chain increases the melting point or softening point of the alkyldiamine tetraalkoxylate surfactant.

Preferably the alkyldiamine tetraalkoxylate surfactant comprises a compound of formula (III) as defined above in which X and Y are integers from 0 to 150, provided X+Y is greater than or equal to 50. In a particularly preferred embodiment A is propylene, B is ethylene, X is 10 to 30 and Y is 50 to 150.

The water soluble or water dispersible granules may be prepared in accordance with standard methods known to the art, such as pan or drum granulation, extrusion, fluid bed or spray drying, or compaction or tabletting. The solid granules have the advantages of allowing high concentrations of active and surfactant, improved storagability and transportability, ease of measuring quantities of compositions and of cleaning of spills, and other advantages generally associated with solid formulations.

It has also been surprisingly found that the surfactant according to the invention can be used in conjunction with an alkyl glycoside or alkylpolyglycoside surfactant. In addition to acting as a hydrotrope for the alkyldiamine tetraalkoxylate surfactant, and thereby improving the compatibility of the alkyldiamine tetraalkoxylate surfactant with the glyphosate herbicide, the alkylglycoside or alkylpolyglycoside surfactant exhibits a synergistic effect with the alkyldiamine tetraalkoxylate surfactant to provide a glyphosate composition having an activity comparable to a glyphosate composition comprising the standard ethoxylated tallow amine surfactant. It has also been unexpectedly found that the presence of the alkyldiamine tetraalkoxylate surfactant with the alkylglycoside or alkylpolyglycoside surfactant reduces the foaming characteristics of the alkylglycoside or alkylpolyglycoside surfactant.

Accordingly in a further aspect of the present invention there is provided a herbicide composition comprising N-phosphonomethylglycine and/or a salt thereof, an alkyldiamine tetraalkoxylate surfactant, and an alkylglycoside or alkylpolyglycoside surfactant.

The terms "alkylglycoside" and "alkylpolyglycoside" as used herein refer to alkylglycosides of glucose or other monosaccharides, or disaccharides, for example, sucrose, or of polysaccharides. These may be obtained by reaction of alkanols with the mono, di or polysaccharides. The term also includes surfactants prepared from mixtures of monosaccharides and disaccharides, as well as from mixtures of alkanols. Commercially available alkylglycosides and alkylpolyglycosides are generally the product of the reaction of glucose with a mixture of alkanols containing 8 to 10 carbon atoms. The number of glycoside units per molecule (i.e. the DG ratio), can vary.

Examples of suitable alkylglycoside or alkylpolyglycoside surfactants suitable for use in accordance with this aspect of the invention include ATPLUS 450, ATPLUS 258, ATPLUS 3001 A (Imperial Chemical Industries PLC), ECOTERIC AS10, ALKADET 15 (ICI Australia), Triton BG (Union Carbide), APG 300, APG 225 (Henkel), Staley APG 91-3, Staley APG 23-1 and Staley APG 23-3 (Staley Corporation)

In order to reduce compatibility problems with the glyphosate herbicide it is preferable for the weight ratio of alkylglycoside or alkylpolyglycoside surfactant to alkyldiamine tetraalkoxylate surfactant to be between 1.2:1 and 2:1, more preferably about 1.5:1. It is preferred that the combination of alkyl glycoside or alkyl polyglycoside surfactants and alkyldiamine tetraalkoxylate surfactants is used in glyphosate compositions containing less than 400 g/L, more preferably less than 360 g/L of glyphosate acid equivalent. For compositions containing a higher concentration of glyphosate it is preferable to use an alkyldiamine tetraalkoxylate of formula III.

It has been found that decreasing the size of the oxyalkylene polymer or block copolymer chain to improve compatibility with the glyphosate herbicide can result in a lowering of the efficacy of a glyphosate herbicide, compared with an equivalent formulation in which the standard ethoxylated tallow amine surfactant is used. However it has been unexpectedly found that the use of an alkylglycoside or alkylpolyglycoside surfactant in combination with such an alkylamine tetraalkoxylate surfactant can bring the activity of the composition up to the level of the standard formulation. The combination of an alkyldiamine tetraalkoxylate surfactant and an alkylglycoside or alkylpolyglycoside surfactant as described above is novel and represents a further aspect of the present invention.

The compositions of the present invention may be formulated as dusts, granular compositions, liquid emulsions or liquid concentrates. The surfactant may also be added to a spray tank solution of glyphosate, i.e.: be applied as a tank added solution. The compositions of the present invention may contain alkyldiamine tetraalkoxylate in an amount of up to about 90% of the weight of glyphosate free acid equivalent present in the formulation.

For use of alkyldiamine tetraalkoxylates as tank added adjuvants there is essentially no upper limit on the amount of surfactant which may be added but typically a surfactant would be used in an amount from 0.025–0.6 kg per ha (on an active surfactant basis) depending on the strength of the glyphosate used.

The compositions of the present invention may be used in the control or eradication of unwanted plants or vegetation by application to a locus where control is desired. Normally this would be on the foliage of the weed pests to be eradicated. Accordingly in yet another aspect of the present invention there is provided a method for controlling or eradicating unwanted plants or vegetation including the step of applying to a locus where control or eradication is desired a phytotoxic amount of a herbicidal composition according to the invention described above.

The composition according to the invention will generally be diluted in water before being sprayed or applied in another known manner on the plant species to be treated. The dilution may be such that conventional spraying of 50–600 L/ha provides 0.125 to 3 kg of glyphosate acid equivalent per hectare. Spray solutions for controlled drop spraying are more concentrated than for other applications.

The phytoactivity of herbicidal compositions also depends on the quantity of glyphosate used for treating the particular plant species; thus, the quantity of composition used is usually expressed in gram glyphosate acid equivalents per hectare. It has been found that 200–600 grams acid equivalent per hectare have provided the most significant results.

The compositions of the present invention may also contain other conventional adjuvants normally formulated with glyphosate formulations such as anti-foaming agents, thickeners, heat stabilizers, ultraviolet absorbers, dispersants and fertilizers, and other agriculturally acceptable materials, including fillers, such as talc, diatomaceous earth and the like, and diluents, such as water. The compositions may also contain additional surfactant adjuvants having low aquatic toxicity, provided the presence of such surfactants does not reduce the efficacy of the herbicidal compositions below acceptable levels.

For solid glyphosate compositions where the adjuvant is built-in an alkyldiamine tetraalkoxylate of high molecular weight is preferably used. The surfactant composition may be used up to a level of 100% by weight of glyphosphate present as free acid equivalent but more typically at less than 35%.

The invention will now be described with reference to the following examples. However it is to be understood that the particularity of the following examples is not to supersede the generality of the preceding description of the invention.

The invention will now be described with reference to the accompanying examples and drawings which illustrate some preferred embodiments of the invention and some comparisons with commercial formulations. However it is to be understood that the particularity of the following description is not to supersede the generality of the preceding description of the invention.

(comparative example) and a standard tallow amine ethoxylate based formulation with the compositions of Examples 6, 7 and 8 on Ryegrass.

Figure 3:
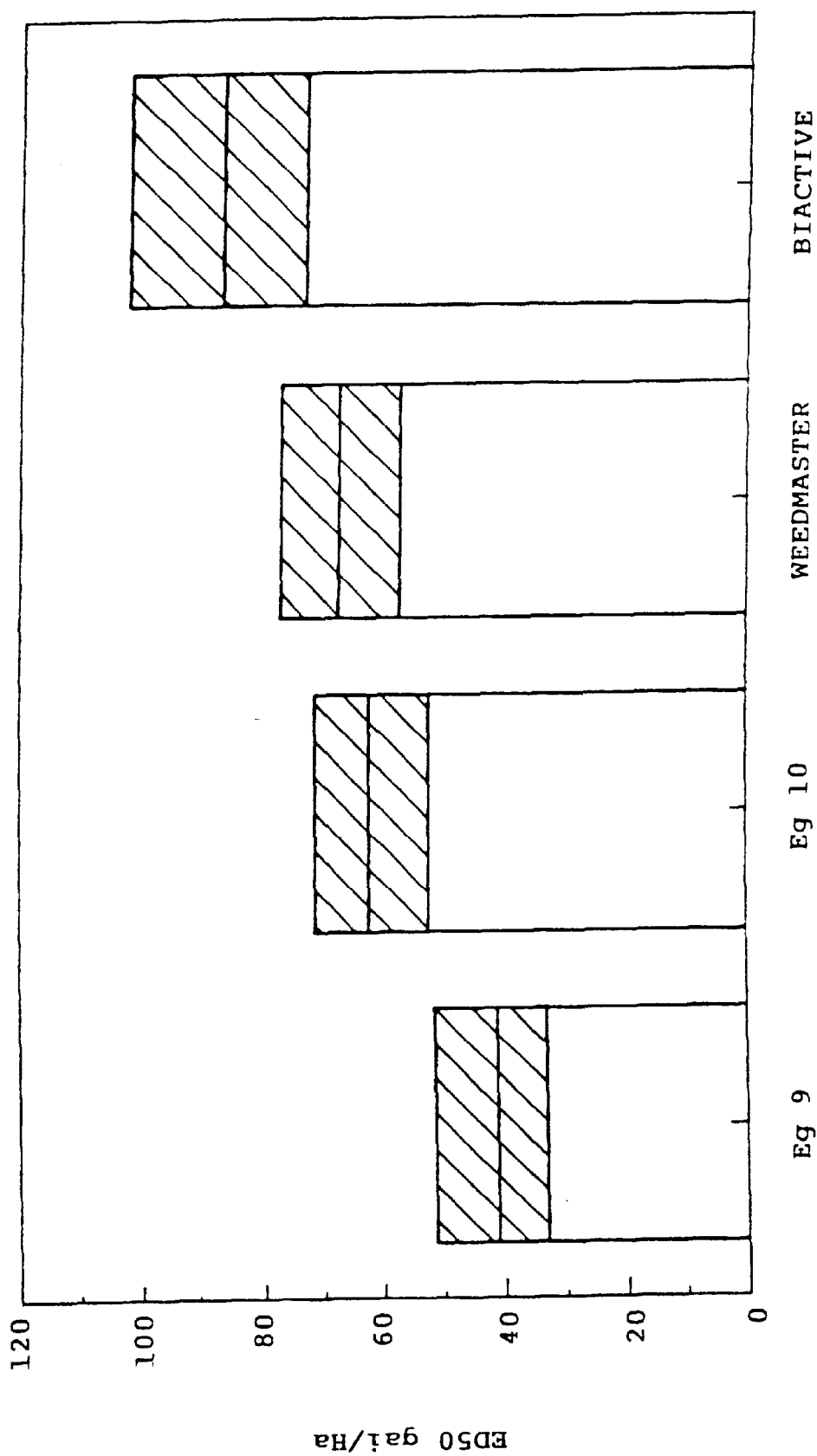

FIG. 3 is a comparison of the calculated $ED_{50}$ values (95% confidence intervals shown by shading) for the composition of Examples 9 and 10 with two commercially available solid formulations on Ryegrass.

Figure 4:
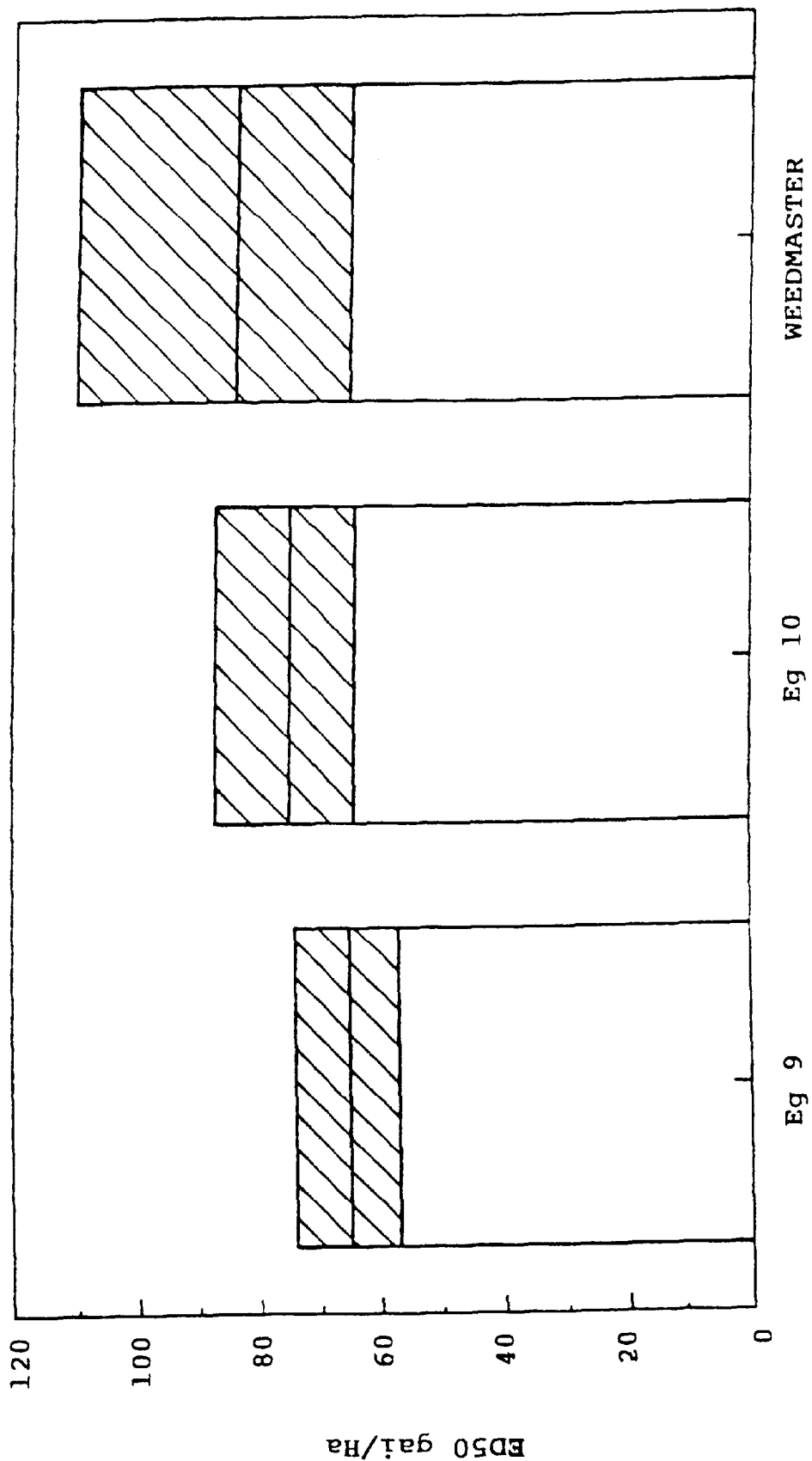

FIG. 4 is a comparison of the calculated $ED_{50}$ values 95% confidence intervals shown by shading) for the compositions of Examples 9 and 10 on the broadleaf plant Canola (*Brassica napus L.*)

Figure 5:
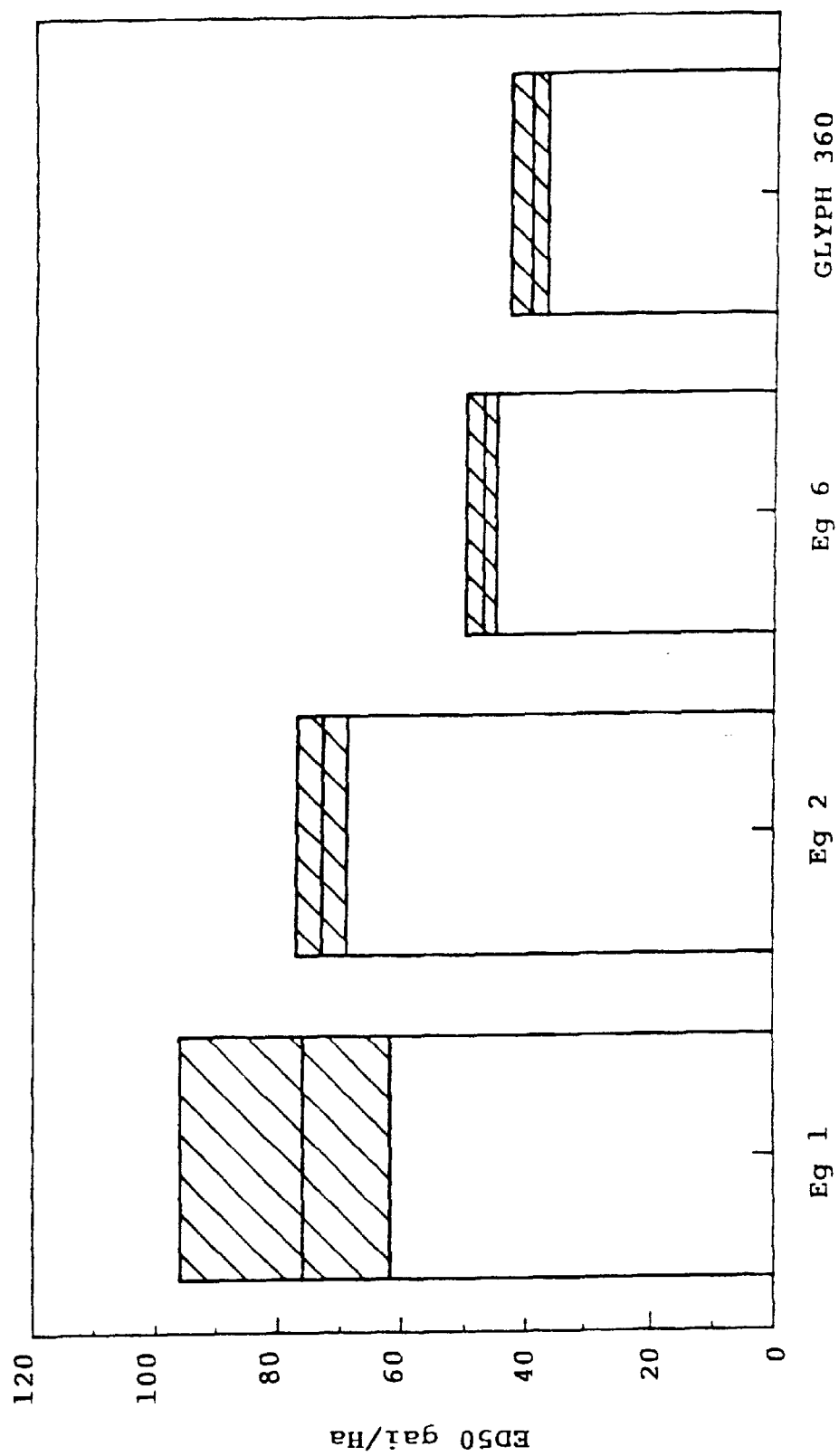

FIG. 5 is a comparison of the calculated $ED_{50}$ values (95% confidence intervals shown by shading) for the compositions of Examples 1, 2 and 6 on Canola

EXAMPLES

Example 1

A 360 g/L formulation of glyphosate present as the isopropylamine salt is formulated as follows:

| Glyphosate isopropylamine salt (60% w/w) | 810 g/L |
| TERIC 170 | 170 |
| Water | to volume. |

(TERIC 170 is a commercially available compound of formula IV where x is 1 and y is 4 as indicated in Table 1.)

Figure 1:
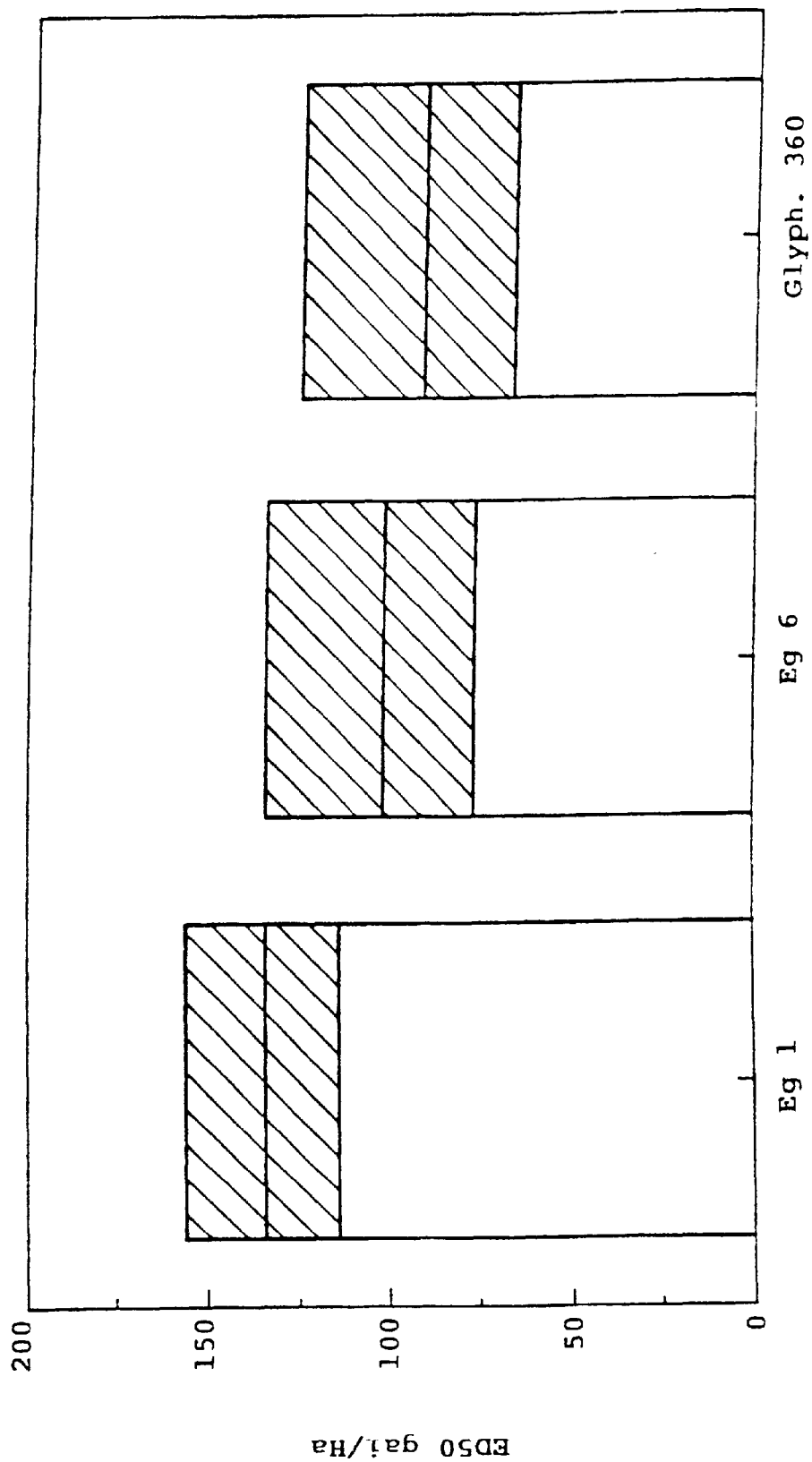
FIG. 1 is a comparison of the calculated $ED_{50}$ values (95% confidence intervals shown by shading) for the compositions of Examples 1 and 6, and the commercial tallow amine ethoxylate based product (referred to the figure as "Glyph 360") on the grass weed, Ryegrass (*Lolium rigidum*).

The acute $EC_{50}$ aquatic toxicity data for TERIC 170 on *Daphnia carinata* is shown in table 2 and the bio-efficacy relative to the standard tallow amine ethoxylate formulation using a similar level of surfactant is shown on Table 3 and in another trial on Table 8. The relative bio-efficacy is also shown in FIG. 1 and FIG. 5. The data from FIG. 1 indicates that the TERIC 170 is comparable to the tallow amine ethoxylate on Ryegrass. TERIC 170 shows greatly reduced acute aquatic toxicity compared to tallow amine ethoxylate.

Example 2

A 360 g/L formulation of glyphosate present as the isopropylamine salt is formulated as follows:

| Glyphosate isopropylamine salt (60% w/w) | 810 g/L |
| TERIC 171 | 170 |
| Water | to volume. |

(TERIC 171 is a commercially available compound of formula IV where x is 12 and y is 4 as indicated in Table 1.)

The bio-efficacy relative to the standard tallow amine ethoxylate formulation is shown on Table 8. The relative bio-efficacy is also shown in FIG. 5. The acute aquatic toxicity of the formulation is greatly reduced relative to the standard tallow amine ethoxylate formulation with TERIC 171.

Example 3

A 360 g/L formulation of glyphosate present as the isopropylamine salt is formulated as follows.

| Glyphosate isopropylamine salt (60% w/w) | 810 g/L |
| TERIC 172 | 170 |
| Water | to volume. |

(TERIC 172 is a commercially available compound of formula IV where x is 3 and y is 4 as indicated in Table 1.)

Example 4

(Comparative example)

A 360 g/L formulation of glyphosate present as the isopropylamine salt may is formulated as follows:

| Glyphosate isopropylamine salt (60% w/w) | 810 g/L |
| ATPLUS 3001A | 243 |
| Water | to volume. |

(ATPLUS 3001A is a commercially available alkylpolyglucoside surfactant as indicated in Table 1.) The level of active surfactant present is 170 g/L.

Figure 2:
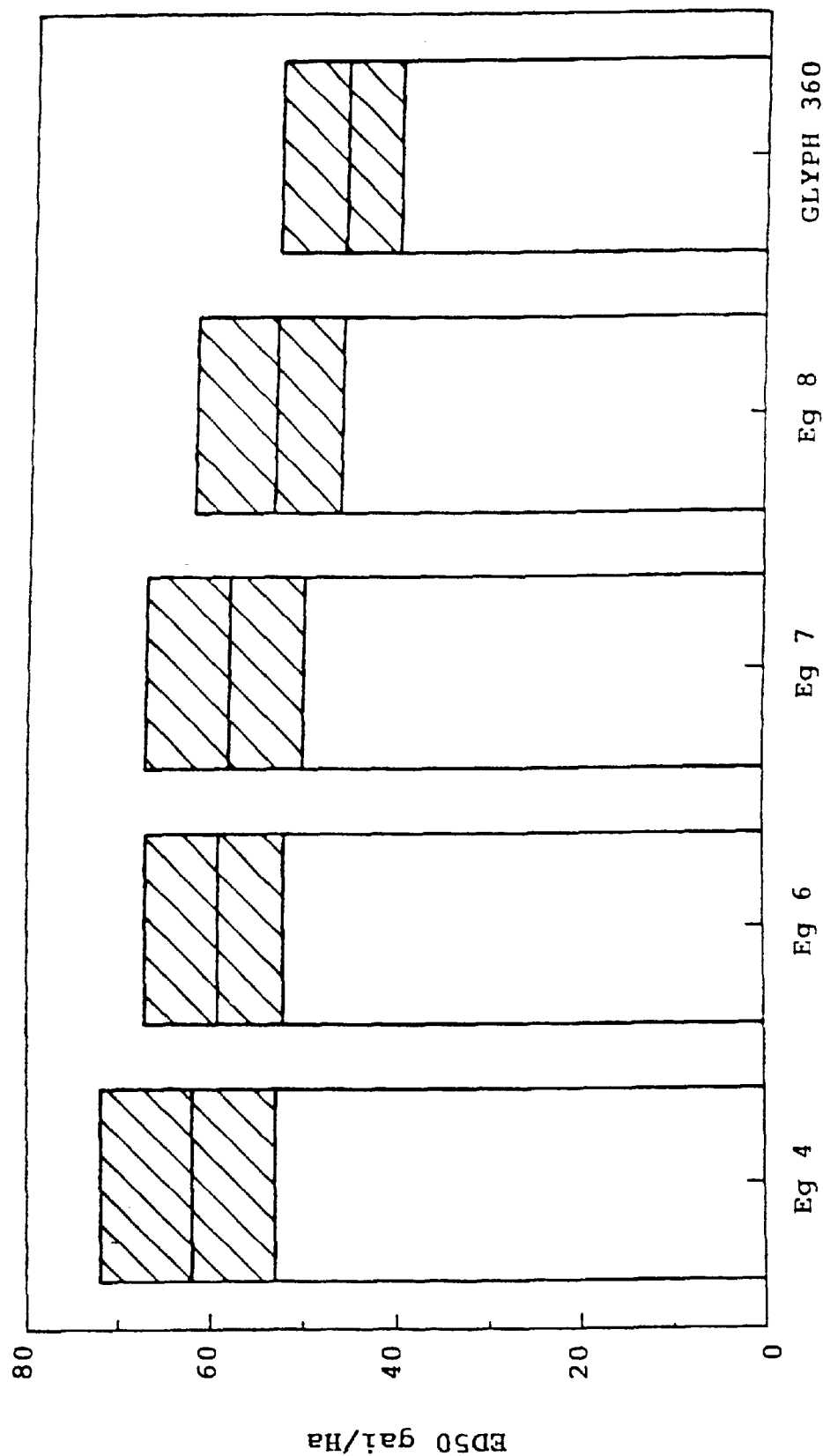
FIG. 2 is a comparison of the $ED_{50}$ values (95% confidence intervals shown by shading) for Example 4

The acute $EC_{50}$ aquatic toxicity data for ATPLUS 3001A on *Daphnia carinata* is shown in Table 2 and the bio-efficacy compared to the standard tallow amine ethoxylate formulation is shown on Table 4. The relative bio-efficacy is also shown in FIG. 2. ATPLUS 3001A has a higher acute aquatic toxicity than the alkyldiamine tetraalkoxylates.

Example 5

A 360 g/L formulation of glyphosate present as the isopropylamine salt is formulated as follows:

| Glyphosate isopropylamine salt (60% w/w) | 810 g/L |
| ATPLUS 436 | 213 |
| Water | to volume. |

(ATPLUS 436 is a commercially available surfactant as indicated in Table 1.) The active surfactant level present in the formulation is 170 g/L.

The acute $EC_{50}$ aquatic toxicity data for ATPLUS 436 in the above formulation on *Daphnia carinata, Litoria Lesueuri* and *oncorhynchus mykiss* is shown in Table 2. The bio-efficacy compared to the standard tallow amine ethoxylate formulation in glasshouse evaluations is shown on Tables 5A and 5B. The results indicate no significant difference in efficacy when compared to the standard tallow amine ethoxylate when used at 360 g/L. The aquatic toxicity of the formulation using ATPLUS 436 is however significantly reduced.

Example 6

A 360 g/L formulation of glyphosate present as the isopropylamine salt is formulated as follows.

| Glyphosate isopropylamine salt (60% w/w) | 810 g/L |
| DS 2529 | 206 |
| Water | to volume. |

(DS 2529 is a blend of TERIC 170 and ATPLUS 3001A as indicated in Table 1.)

The acute $EC_{50}$ aquatic toxicity data for the above composition on *Daphnia carinata, Litoria Lesueuri* and *oncorhynchus mykiss* is shown in Table 2. The bio-efficacy compared to the standard tallow amine ethoxylate formulation and TERIC 170 on ryegrass is shown on Table 3 and with Canola on Table 8. Comparison with ATPLUS 3001A is shown in Table 4. Its relative bioefficacy is shown in FIG. 1, FIG. 2 and FIG. 3. These results indicate that the combination of ATPLUS 3001A and TERIC 170 has resulted in same or better performance than the ATPLUS 3001A used alone at the same rate. The results also indicate that the combination of ATPLUS 3001A and TERIC 170 has resulted in an efficacy result better than TERIC 170 alone while at the same time markedly improving the aquatic toxicity profile of the formulation.

Example 7

A 360 g/L formulation of glyphosate present as the isopropylamine salt is formulated as follows:

| | |
|---|---|
| Glyphosate isopropylamine salt (60% w/w) | 810 g/L |
| DS 2547 | 192 |
| Water | to volume. |

(DS 2547 is a blend of TERIC 170 and ATPLUS 3001A as indicated in Table 1.)

The bio-efficacy compared to the standard tallow amine ethoxylate is shown on Table 4 and its relative bioefficacy is shown in FIG. 2. These results indicate that the combination of ATPLUS 3001A and TERIC 170 has resulted in better performance on these ryegrass weeds than the ATPLUS 3001A used alone at the same rate. The results also indicate that the combination of ATPLUS 3001A and TERIC 170 has resulted in an efficacy result better than TERIC 170 alone while at the same time it will markedly improve the aquatic toxicity profile of the formulation.

Example 8

A 360 g/L formulation of glyphosate present as the isopropylamine salt is formulated as follows:

| | |
|---|---|
| Glyphosate isopropylamine salt (60% w/w) | 810 g/L |
| DS 2548 | 177 |
| Water | to volume. |

(DS 2548 is as indicated in Table 1.)

The bio-efficacy is shown on Table 4 and its relative bioefficacy is shown in FIG. 2. These results indicate that the combination of ATPLUS 3001A and TERIC 170 has resulted in better performance than the ATPLUS 3001A used alone at the same rate. The results also indicate that the combination of ATPLUS 3001A and TERIC 170 has resulted in an efficacy result better than TERIC 170 alone while at the same time markedly improving the aquatic toxicity profile of the formulation.

Example 9

A solid granular formulation of glyphosate present as the monoammonium salt is formulated as follows:

| | |
|---|---|
| Glyphosate ammonium salt (96% w/w) | 734 g/kg |
| SYNPERONIC T/707 | 217 |
| Ammonium sulphate | 49 |

(SYNPERONIC T/707 is a compound of formula IV where x is approximately 16 and y is 50 as indicated in Table 1.)

The acute $EC_{50}$ aquatic toxicity data for *Daphnia carinata* is shown in Table 2 and its bio-efficacy relative to the commercially available solid formulations of Weedmaster™ (Nufarm) and Biactive™(Monsanto) on grass and broadleaf weed species is shown in Tables 6 and 7. Weedmaster contains a urea-nonionic surfactant complex while Biactive is believed to contain a blend of alkylquaternaryaminealkoxylate and polysorbate surfactants. The relative bio-efficacy of the product is shown in FIGS. 3 and 4. From the data SYNPERONIC T/707 is significantly more efficacious on grass weeds than the commercial formulations and at least comparable on broadleaf weeds.

Example 10

A solid granular formulation of glyphosate present as the monoammonium salt is formulated as follows:

| | |
|---|---|
| Glyphosate ammonium salt (96% w/w) | 734 g/kg |
| SYNPERONIC T/908 | 217 |
| Ammonium sulphate | 49 |

(SYNPERONIC T/908 is a compound of formula IV where x is approximately 16 and y is 50 as indicated in Table 1.)

The acute $EC_{50}$ aquatic toxicity data for *Daphnia carinata* is shown in Table 2 and its bio-efficacy compared to the commercially available solid formulations as described in Example 9 on broadleaf and grass weed species is shown in Tables 6 and 7. The relative bio-efficacy of the product is shown in FIGS. 3 and 4. The data indicates that the SYNPERONIC T/908 formulation is comparable in efficacy to Weedmaster and significantly better than Biactive in the ryegrass weeds. The SYNPERONIC T/908 formulation is at least comparable with Weedmaster formulation on the Canola weeds. The formulation using SYNPERONIC T/908 will be expected to have a significantly better aquatic toxicity profile than the Weedmaster sample tested based on comparative results for the surfactant type used.

TABLE 1

Product MW - Compositions

| Product | No mol PO | No mol EO | Base | % Surfactant | MW |
|---|---|---|---|---|---|
| TERIC 170 | 4 | 16 | Ethylene diamine | 100 | 996 |
| TERIC 171 | 8 | 16 | Ethylene diamine | 100 | 1228 |
| TERIC 172 | 12 | 16 | Ethylene diamine | 100 | 1460 |
| TERIC 173 | 16 | 16 | Ethylene diamine | 100 | 1692 |
| ATPLUS 3001A | — | — | C8–C10 alcohol | 70 | — |
| ATPLUS 436 (DS 2320) | — | — | Blend: ATPLUS 3001A TERIC 173 | 68 32 | — |
| DS 2529 | | | Blend: ATPLUS 3001A | 59 | — |

TABLE 1-continued

Product MW - Compositions

| Product | No mol PO | No mol EO | Base | % Surfactant | MW |
|---|---|---|---|---|---|
| DS 2547 | | | TERIC 170 | 41 | — |
| | | | Blend: ATPLUS 3001A | 38 | — |
| | | | TERIC 170 | 62 | — |
| DS 2548 | | | Blend: ATPLUS 3001A | 14 | — |
| | | | TERIC 170 | 86 | — |
| SYNPERONIC T/707 (DS 2533) | 63 | 200 | Ethylene diamine | 100 | 12500 |
| SYNPERONIC T/908 (DS 2534) | 90 | 472 | Ethylene diamine | 100 | 26000 |

TABLE 2

Aquatic Toxicity Data EC50 (ppm)

| | Aquatic Species | | |
|---|---|---|---|
| Product | Water Flea (*Daphnia Carinata*) | Tadpole (# *Litoria Lesueuri* *Litoria ewingi*) | Rainbow Trout (*oncorhynchus mykiss*) |
| TERIC 170 | 766 | — | — |
| TERIC 173 | 2518 | — | — |
| ATPLUS 3001A | 79 | — | — |
| ATPLUS 436 In glyphosate 360 g/L | 210 | 2563# | 806 |
| DS 2529 In glyphosate 360 g/L | 490 | 3230* | 1080 |
| SYNPERONIC T/707 | >100,000 | — | — |
| SYNPERONIC T/908 | 93,000 | — | — |

TABLE 3

Bio-efficacy data for Glyphosate 360 g/L Formulations

| | | Ryegrass (*Lolium rigidum*) ED50 gai/ha 95% Ci* | | |
|---|---|---|---|---|
| Product | Example No. | ED50 | Lower | Upper |
| TERIC 170 | 1 | 134 | 114 | 156 |
| DS 2529 | 6 | 101 | 76 | 134 |
| Glyph. 360 | — | 91 | 66 | 125 |

*Ci-Confidence interval calculated for the ED50

TABLE 4

Bio-efficacy data for Glyphosate 360 g/L Formulations

| | | Ryegrass (*Lolium rigidum*) ED50 gai/ha 95% Ci* | | |
|---|---|---|---|---|
| Product | Example No. | ED50 | Lower | Upper |
| DS 2529 | 6 | 59 | 52 | 67 |
| ATPLUS 3001A | 4 | 62 | 53 | 72 |
| DS 2547 | 7 | 58 | 50 | 67 |
| DS 2548 | 8 | 53 | 46 | 62 |
| GLYPH 360 | — | 46 | 40 | 53 |

*Ci-Confidence interval calculated for the ED50

TABLE 5A

RESULTS SUMMARY
Annual ryegrass

| Adjuvant | 9 DAT α | | | 27 DAT α | | | 28 DAT β | | |
|---|---|---|---|---|---|---|---|---|---|
| | $I_{50}$ L/ha | L | U | $I_{50}$ L/ha | L | U | $I_{50}$ L/ha | L | U |
| Standard* | 0.771 a | 0.629 | 0.913 | 0.089 a | 0.074 | 0.103 | 0.058 ab | 0.046 | 0.069 |
| ATPLUS 436 | 0.969 a | 0.712 | 1.225 | 0.099 ab | 0.090 | 0.109 | 0.055 ab | 0.042 | 0.067 |

*Standard tallow amine ethoxylate sold under trade mark ATLAS G3780A
DAT = days after treatment
α = visual count
β = fresh weight
L and U denote lower and upper 95% confidence limits of the value $I_{50}$
$I_{50}$ is the dose in L/ha that will give a 50% score on the rating system used. This is an approximation to the dose that will give 50% control of the sprayed plants.
Values followed by the same letter do not differ significantly at the 95% confidence level.

TABLE 5B

Paterson's curse

| Adjuvant | 9 DAT α | | | 27 DAT α | | | 28 DAT β | | |
|---|---|---|---|---|---|---|---|---|---|
| | $I_{50}$ L/ha | L | U | $I_{50}$ L/ha | L | U | $I_{50}$ L/ha | L | U |
| Standard* | 0.366 a | 0.269 | 0.463 | 0.152 abc | 0.116 | 0.188 | 0.104 ab | 0.055 | 0.153 |
| ATPLUS 436 | 0.540 a | 0.320 | 0.760 | 0.207 c | 0.169 | 0.245 | 0.109 b | 0.082 | 0.135 |

*Standard tallow amine ethoxylate sold under trade mark ATLAS G3780A
DAT = days after treatment
α = visual content
β = fresh weight
L and U denote lower and upper 95% confidence limits of the value $I_{50}$
$I_{50}$ is the dose in L/ha that will give a 50% score on the rating system used. This is an approximation to the dose that will give 50% control of the sprayed plants.
Values followed by the same letter do not differ significantly at the 95% confidence level.

TABLE 6

Bio-efficacy data for Ammonium Glyphosate Formulations

| | | Ryegrass (*Lolium rigidum*) ED50 gai/ha 95% Ci* | | |
|---|---|---|---|---|
| Product | Example No. | ED50 | Lower | Upper |
| SYNPERONIC T/707 | 9 | 41 | 33 | 51 |
| SYNPERONIC T/908 | 10 | 62 | 52 | 73 |
| WEEDMASTER ® | — | 67 | 57 | 77 |
| BIACTIVE ® | — | 87 | 73 | 102 |

*Ci-Confidence interval calculated for the ED50

TABLE 7

Bio-efficacy data for Ammonium Glyphosate Formulations

| | | Canola (*Brassica napus L.*) ED50 gai/ha 95% Ci* | | |
|---|---|---|---|---|
| Product | Example No. | ED50 | Lower | Upper |
| SYNPERONIC T/707 | 9 | 65$^a$ | 57 | 74 |
| SYNPERONIC T/908 | 10 | 75$^{ab}$ | 64 | 87 |
| WEEDMASTER ® | — | 84$^{ab}$ | 65 | 110 |

*Ci-Confidence interval calculated for the ED50

TABLE 8

Bio-efficacy data for Glyphosate 360 g/L Formulations

| | | Canola (*Brassica napus L.*) ED50 gai/ha 95% Ci* | | |
|---|---|---|---|---|
| Product | Example No. | ED50 | Lower | Upper |
| TERIC 170 | 1 | 76 | 62 | 96 |
| TERIC 171 | 2 | 73 | 69 | 77 |
| DS 2529 | 6 | 47 | 45 | 50 |
| GLYPH 360 | — | 40 | 37 | 43 |

*Ci-Confidence interval calculated for the ED50

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more said steps or features.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The claims defining the invention are as follows:

1. A herbicidal composition comprising N-phosphonomethylglycine and/or a salt thereof and an alkyldiamine tetraalkoxylate surfactant.

2. A herbicidal composition according to claim 1 wherein the alkyldiamine tetraalkoxy surfactant comprises a compound of formula (I):

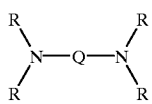

(I)

where Q is a linear or branched $C_1$–$C_6$ alkylene, and
each R is independently selected from oxylalkylene polymer or block copolymer chains.

3. A herbicidal composition according to claim 2 wherein the alkyldiamine tetraalkoxylate surfactant comprises a compound of formula (III):

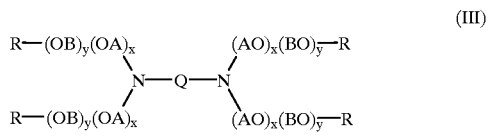

(III)

wherein A and B are different $C_2$–$C_4$ alkylene groups,
R is H or $C_1$–$C_6$ alkyl, and
X and Y are integers from 0 to 150, provided X and Y are not both zero.

4. A herbicidal composition according to claim 3 wherein A is propylene and B is ethylene, or A is ethylene and B is propylene.

5. A herbicidal composition according to claim 4 wherein:
A is propylene
B is ethylene
R is hydrogen,
X is 1 to 3, Y is 3 to 5, provided X+Y≦6.

6. A herbicidal composition according to claim 5 wherein X is 1 and Y is 4.

7. A herbicidal composition according to claim 1 in the form of a water dispersible or water soluble granule.

8. A herbicidal composition according to claim 7 comprising a non-hygroscopic salt of N-phosphonomethylglycine.

9. A herbicidal composition according to claim 8 wherein the salt of N-phosphonomethylglycine is an ammonium salt.

10. A herbicidal composition according to claim 8 or claim 9 wherein the alkyldiamine tetraalkoxylate surfactant has a melting point or softening point greater than 45° C.

11. A herbicidal composition according to claim 10 wherein the alkyldiamine tetraalkoxylate surfactant has a melting point or softening point greater than 50° C.

12. A herbicidal composition according to claim 1 further comprising an alkylglycoside or alkylpolyglycoside surfactant.

13. A herbicidal composition according to claim 12 wherein the weight ratio of alkylglycoside or alkylpolyglycoside surfactant to alkyldiamine tetraalkoxylate surfactant is between 1.2:1 and 2:1.

14. A herbicidal composition according to claim 13 wherein the ratio is about 1.5:1.

15. A method for preparing a herbicidal composition comprising admixing N-phosphonomethylglycine and/or a salt thereof with a surfactant composition comprising an alkyldiamine tetraalkoxylate surfactant and an alkylglycoside or alkylpolyglycoside surfactant.

16. The method according to claim 15 wherein the weight ratio of alkylglycoside or alkylpolyglycoside surfactant to alkyldiamine tetraalkoxylate is between 1.2:1 and 2:1.

17. A method for preparing a herbicidal composition comprising admixing N-phosphonomethylglycine and/or a salt thereof with an alkyldiamine tetraalkoxylate surfactant.

18. A method of controlling or eradicating unwanted plants or vegetation including the step of applying to a locus where control or eradication is desired a phytotoxic amount of a composition according to claim 1.

* * * * *